United States Patent [19]

Fujii

[11] Patent Number: 5,213,107

[45] Date of Patent: May 25, 1993

[54] PORTABLE ELECTROCARDIOGRAPH

[75] Inventor: Ryoichi Fujii, Soraku, Japan

[73] Assignee: Sharp Kabushiki Kaisha, Osaka, Japan

[21] Appl. No.: 675,352

[22] Filed: Mar. 25, 1991

[30] Foreign Application Priority Data

Apr. 2, 1990 [JP] Japan ................................ 2-88579

[51] Int. Cl.[5] .......................................... A61B 5/0432
[52] U.S. Cl. ................................................ 128/710
[58] Field of Search ......................... 128/702-704,
128/709-712, 696-695, 731, 734; 364/413.06

[56] References Cited

U.S. PATENT DOCUMENTS

| | | | |
|---|---|---|---|
| 4,096,854 | 6/1978 | Perica et al. | 128/690 |
| 4,622,979 | 11/1986 | Katchis et al. | 128/702 |
| 4,958,641 | 9/1990 | Digby et al. | 128/702 |

Primary Examiner—Lee S. Cohen
Assistant Examiner—Jeffrey R. Jastrzab
Attorney, Agent, or Firm—David G. Conlin; George W. Neuner

[57] ABSTRACT

A portable electrocardiograph capable of providing a low electricity consumption rate by controlling an electric power supply from a power supply device, the portable electrocardiograph includes a unit for detecting electrocardiographic signals and for converting the electrocardiographic signals into electrocardiographic complex data, a unit connected with the detecting unit for displaying the electrocardiographic complex data, and a unit for controlling an electric power supply for either the detecting unit or the displaying unit in accordance with a predetermined mode so that the electric power supply from the power supply device is continued during a predetermined time period.

13 Claims, 7 Drawing Sheets

Fig. 3

IMMEDIATELY AFTER
tTH DATA IS STORED
(t<n)

| ADDRESS | DATA |
|---|---|
| 0 | $X_0$ |
| 1 | $X_1$ |
| ---- | ---- |
| t-1 | $X_{t-1}$ |
| t | $X_t$ |
| t+1 | 0 |
| ---- | ---- |
| n-1 | 0 |

IMMEDIATELY AFTER MEASUREMENT KEY IS OPERATED ↓

NEWEST DATA ↕

Fig. 4

IMMEDIATELY AFTER
n+kTH DATA IS STORED
(k<n)

| ADDRESS | DATA |
|---|---|
| 0 | $X_n$ |
| 1 | $X_n$ |
| ---- | ---- |
| k-1 | $X_{n+k-1}$ |
| k | $X_{n+k}$ |
| k+1 | $X_{n-k+1}$ |
| ---- | ---- |
| n-1 | $X_{n-1}$ |

OLDEST DATA ↓

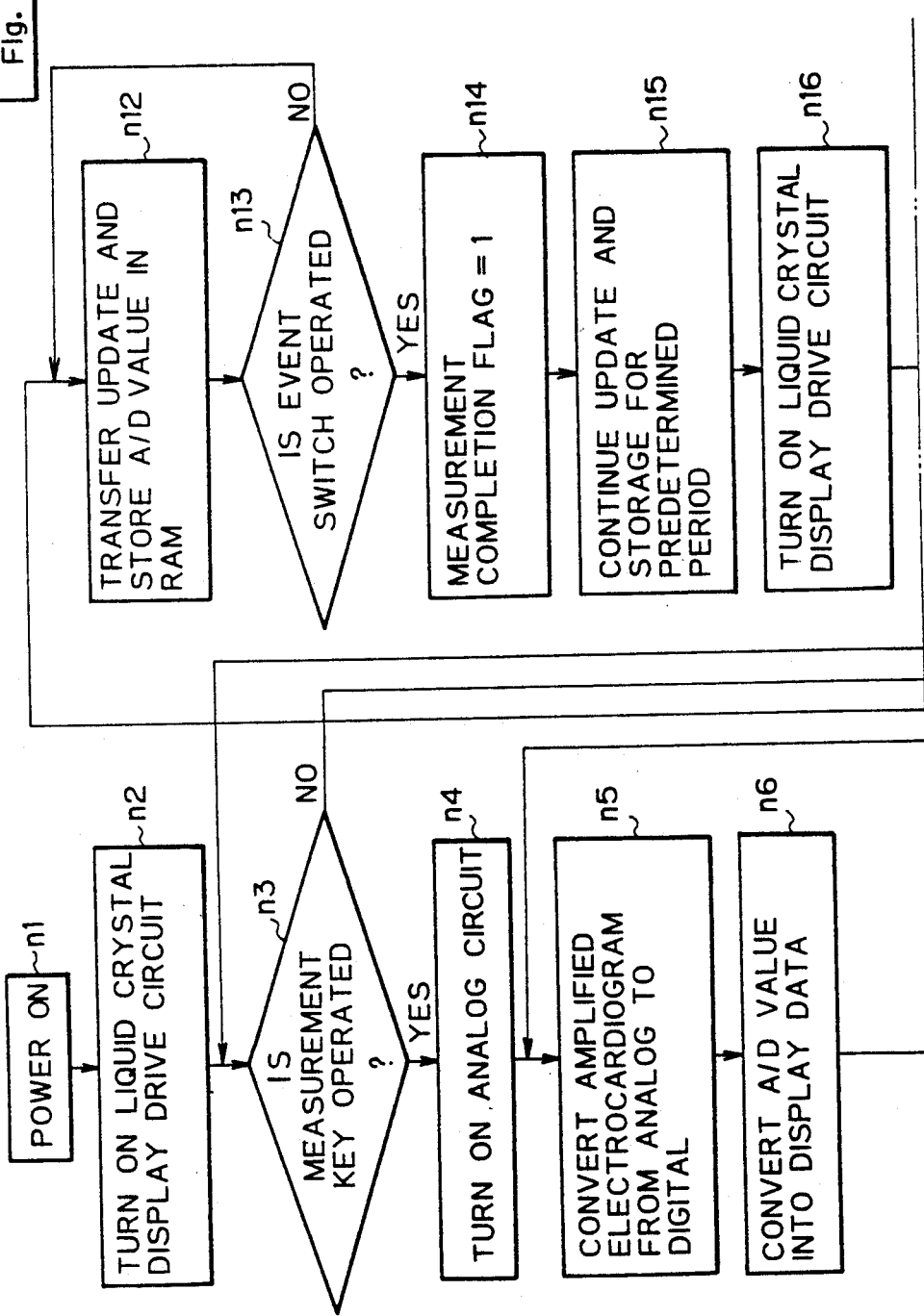

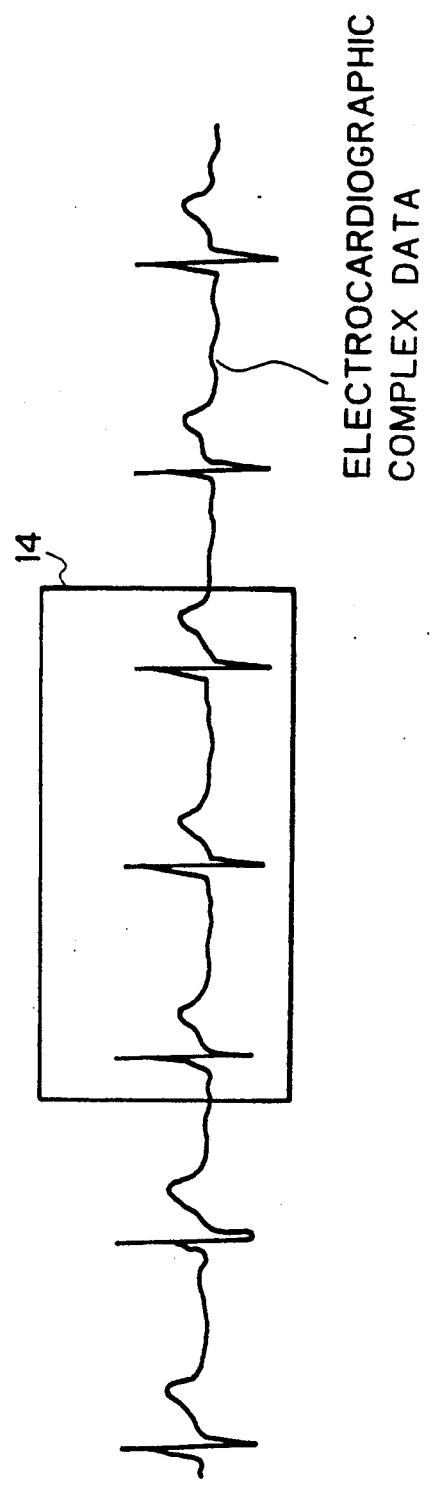

PORTABLE ELECTROCARDIOGRAPH

BACKGROUND OF THE INVENTION

1. Field of the Invention

The present invention relates to an electrocardiograph which is capable of obtaining electrocardiographic complex data, in particular, to a portable electrocardiograph.

2. Description of the Related Art

The inventor of the present invention knows that an around-the-clock continuous recorder which is called a Holter electrocardiograph and which records on a magnetic tape is conventionally used as an electrocardiograph to measure and to watch electrocardiographic complex data when a paroxysm arises in everyday life.

Although the above-mentioned electrocardiograph enables to record electrocardiographic complex data for many hours, it is necessary to replace a recording tape every day and to prepare many recording tapes in a case of angina pectoris decubitus whose frequency of paroxysms is low, and also difficult to immediately read the electrocardiographic complex data regarding the paroxysm.

In order to solve the above-mentioned problems, a portable electrocardiograph with a liquid crystal display, which is adapted to be portably mounted on a part of body of a user of the portable electrocardiograph, capable of storing the electrocardiographic complex data and capable of reproducing the stored electrocardiographic complex data on the liquid crystal display simultaneously is developed.

The inventor of the present invention and his colleagues developed a portable electrocardiograph capable of storing only electrocardiographic complex data before and/or after abnormal things happened with the user's heart. The above-mentioned portable electrocardiograph is disclosed in Japanese Patent Application Laying Open No.Hei 1-238829 and in Japanese Patent Application Laying Open No.Hei 1-123563.

However, any of the above-mention portable electrocardiographs is adapted to measure and display electrocardiographic complex data continuously, thereby a consumption of electric power, in particular the consumpution of the batteries are extensive, therefore the user must replace the battery very frequently in order to activate all functions thereof.

SUMMARY OF THE INVENTION

It is therefore an object of the present invention to provide a portable electrocardiograph which is capable of providing a low electricity consumption rate.

The object of the present invention can be achieved by a portable electrocardiograph capable of providing a low electricity consumption rate by controlling an electric power supply from a power supply device, the portable electrocardiograph includes a unit for detecting electrocardiographic signals and for converting the electrocardiographic signals into electrocardiographic complex data, a unit connected with the detecting unit for displaying the electrocardiographic complex data, and a unit for controlling an electric power supply for either the detecting unit or the displaying unit in accordance with a predetermined mode so that the electric power supply from the power supply device is continued during a predetermined time period.

According to the present invention, at a time when the electrocardiographic complex data are stored in the storing unit, the electricity supply to the displaying unit is stopped and the electrocardiographic complex data is not displayed on the displaying unit. Furthermore, when the electrocardiographic complex data stored in the storing unit are reproduced on the displaying unit, the electricity supply to the detecting unit is stopped and the electrocardiographic signals are not detected. Therefore, the portable electrocardiograph of the present invention enables to reduce a consumption of the electricity substantially.

Preferably, the portable electrocardiograph further comprises a unit connected to the detecting unit for storing the electrocardiographic complex data so that the stored electrocardiographic complex data are displayed on the displaying unit in accordance with the predetermined mode during the predetermined time period.

Further preferably, the predetermined mode is a storage mode for controlling the electric power supply from the power supply device to the displaying unit and for storing the electrocardiographic complex data into the storing unit from the detecting unit.

More preferably, the predetermined mode is a reproduction mode for controlling the electric power supply from the power supply device to the detecting unit and for displaying the electrocardiographic complex data stored in the storing unit on the displaying unit.

The portable electrocardiograph further comprises a unit for supplying the electrocardiographic signals generated in accordance with heart pulsations, and a unit for amplifying the electrocardiographic signals supplied from the supplying unit so that small heart pulsation signals are amplified for detecting any abnormality in the heart pulsations, preferably.

The storing unit is preferably adapted to store information of the heart pulsation in a precedence time period before activating the reproduction mode thereon.

The storing unit preferably consists of a plurality of data areas and a plurality of addresses, each of the addresses being attached with each of the data areas, respectively.

Preferably, the storing unit is so arranged that the electrocardiographic complex data are stored from an area of the plurality of data areas having an address of the plurality addresses to another area of the plurality of data areas having another address of the plurality of addresses sequentially.

The area of the plurality of data areas is preferably an area having zero address, and the another area of the plurality of data areas is the largest data area having address of $n-1$ with the n representing an integer number.

The storing unit is so arranged that the plurality of data areas are overwritten from the data area having the zero address at a time when the electrocardiographic complex data reaches at the largest area having the address $n-1$, preferably.

The storing unit is so arranged that a start position and an end position of the electrocardiographic complex data stored therein are judged by holding a data area in a pointer register, the data area holding the newest data in a measurement of the heart pulsations, preferably.

The object of the present invention also can be achieved by a portable electrocardiograph capable of providing a low electricity consumption rate and adapted to be operated in accordance with an electric power supplied by a power supply device, the portable electrocardiograph having electrodes for detecting electrocardiographic signals, the portable electrocardiograph includes an analog circuit connected with the power supply device for amplifying the electrocardiographic signals detected by the electrodes and for converting the amplified signals into electrocardiographic complex data, a main control circuit connected to the power supply device for receiving the electrocardiographic complex data in a time sequence and for storing dot data developed from the electrocardiographic complex data in display data areas thereof, and a liquid crystal display unit connected to the power supply device for displaying the dot data stored in the display data areas of the main control circuit unit.

According to the present invention, at a time when the dot data are stored in the main control circuit, the electricity supply to the liquid crystal display unit is stopped and the dot data are not displayed on the liquid crystal displaying unit. Furthermore, when the dot data stored in the main control circuit are reproduced on the liquid crystal displaying unit, the electricity supply to the analog circuit is stopped and the electrocardiographic complex data are not detected. Therefore, the portable electrocardiograph of the present invention enables to reduce a consumption of the electricity substantially.

Preferably, the analog circuit includes an electrocardiographic amplifier for amplifying electrocardiographic signals detected by electrodes, an analog/digital converter for sampling the amplified signals at a sampling frequency of a predetermined cycle and for converting the amplified signals into electrocardiographic complex data, and power supply terminals connected to the power supply device.

Further preferably, the main control circuit includes a central processing unit for receiving the electrocardiographic complex data in the time sequence and for developing the electrocardiographic complex data into the dot data to be used for display, a random access memory for storing the dot data in display data areas thereof, peripheral circuit therein, and a power supply terminal connected to the power supply device.

More preferably, the liquid crystal display unit includes a liquid crystal display device, a liquid crystal drive circuit, and a power supply terminal thereof connected to the power supply device.

The random access memory preferably consists of a plurality of display data areas and capable of storing the display dot data in the display data areas so that the display dot data are sequentially transferred to the liquid crystal display drive circuit and the display dot data are displayed in the liquid crystal display device.

The power supply terminal of the analog circuit is preferably connected to the power supply device through a switch which is composed of a software switch adapted to be turned on/off in accordance with a control of the central processing unit, the switch being adapted to be turned on either in a measurement mode or in a measurement start mode and to be turned off in a reproduction mode.

The switch is enable signal terminals of a gate circuit included in the analog circuit, preferably.

The power supply terminal of the liquid crystal display unit is preferably connected to the power supply device through a switch which is composed of a software switch adapted to be turned on/off in accordance with a control of the central processing unit, the switch being adapted to be turned on either in a measurement mode or in a reproduction mode and to be turned off in measurement start mode.

Preferably, the switch is enable signal terminals of a gate circuit which is included in the liquid crystal display circuit.

Further objects and advantages of the present invention will be apparent from the following description of the preferred embodiments of the invention as illustrated in the accompanying drawings.

BRIEF DESCRIPTION OF THE DRAWINGS

FIGS. 3 and 4 show the storage area in a memory of the electrocardiograph shown in FIG. 1;

FIG. 7 illustrates an example of electrocardiographic complex data.

DESCRIPTION OF THE PREFERRED EMBODIMENTS

An embodiment of the present invention will now be described in detail with reference to the accompanied drawings.

Figure 1:
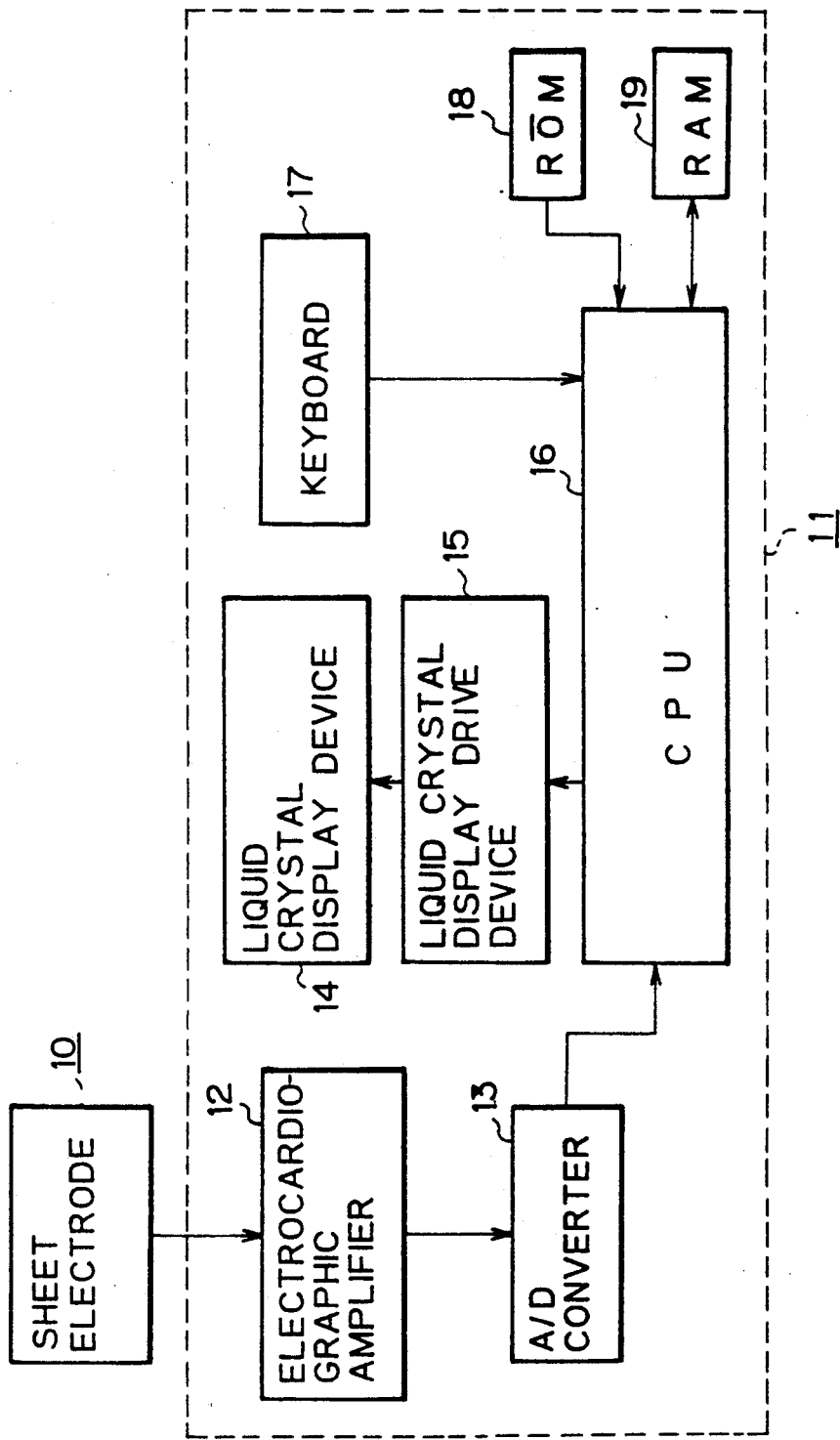
FIG. 1 shows the overall structure of an electrocardiograph of the present invention.

FIG. 1 shows a structure of one embodiment of the electrocardiograph of the present invention.

As shown in FIG. 1, electrodes 10, which are attached to a body of a subject matter and which is adapted to detect electrocardiograms, is connected to an electrocardiograph body 11.

The electrocardiograph body 11 includes an electrocardiographic amplifier 12 for amplifying electrocardiographic signals sent from the electrodes 10, an A/D converter 13 for converting the amplified electrocardiographic signals sent from the electrocardiographic amplifier 12 from analog signals into digital signals, a liquid crystal display device 14, a liquid crystal display drive circuit 15, a CPU 16, a keyboard 17 with various kinds of function keys, a ROM 18 for storing a control program shown in FIG. 6 and a RAM 19 storing an electrocardiographic complex data area, a display data area as well as a work area.

Figure 2:
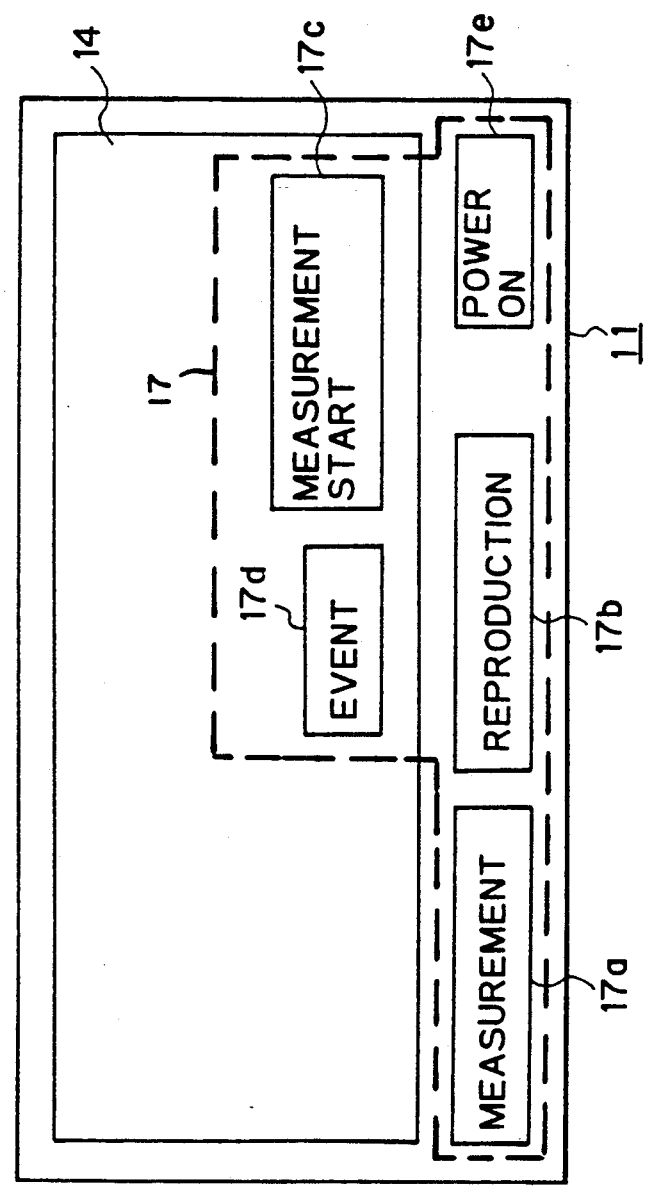
FIG. 2 shows a detailed view of the operational unit of the electrocardiograph shown in FIG. 1.

FIG. 2 shows an operational unit of the electrocardiograph body 11 which includes the liquid crystal display device 14 and the keyboard 17 shown in FIG. 1.

The liquid crystal display device 14 displays measured electrocardiographic complex data as shown in FIG. 7.

The keyboard 17 is provided with a measurement key 17a for designating a mode which displays electrocardiographic complex data detected by the electrodes 10 1 in the liquid crystal display device 14 simultaneously with the measurement without storing the data in the electrocardiographic complex data area of the RAM 19, a reproduction key 17b for designating a mode which reproduces the electrocardiographic complex data stored in the electrocardiographic complex data area of the RAM 19 in the liquid crystal display device 14, a measurement start key 17c for designating a mode which updates and stores the measured electrocardiographic data in the electrocardiographic complex data area of the RAM 19 without displaying the electrocardiographic complex data in the liquid crystal display device 14, an event key 17d for designating a mode which executes an update and a storage for a predetermined period and subsequently stops the measurement, and a power switch 17e.

FIGS. 3 and 4 show the electrocardiographic complex data area of the RAM 19. The A/D converter 13 converts the electrocardiographic signals, which are detected by and received from the electrodes 10, into digital electrocardiographic complex data. The electrocardiographic complex data is fetched in every predetermined sampling time and stored in data areas Xi, each of the data area Xi being addressed with i represented either t or n+k in FIGS. 3 or 4 respectively.

The electrocardiographic complex data are sequentially stored in the data areas from the area with the address 0 to the largest area with the address n−1 shown in FIGS. 3 and 4, and after the electrocardiographic complex data reaches the largest area with the address n−1, the data areas are overwritten from the area 0 in turn.

When the measurement is completed, the start position and the end position of the stored electrocardiographic complex data can be judged by holding the data area in a pointer register (not shown) with the data area holding the newest data in the measurement.

FIG. 3 shows the storage state (address t, data Xt) at a time t is passed after the measurement key is operated. No data is stored in the area t+1 and subsequent areas.

FIG. 4 shows the storage state (address k+1, data Xn−k+1) at a time n+k is passed after an overwriting operation is performed over the capacity of the electrocardiographic judgment data areas. In this state, the data are stored from the oldest data to the newer one in turn in the subsequent areas of the area k+1.

Figure 5:
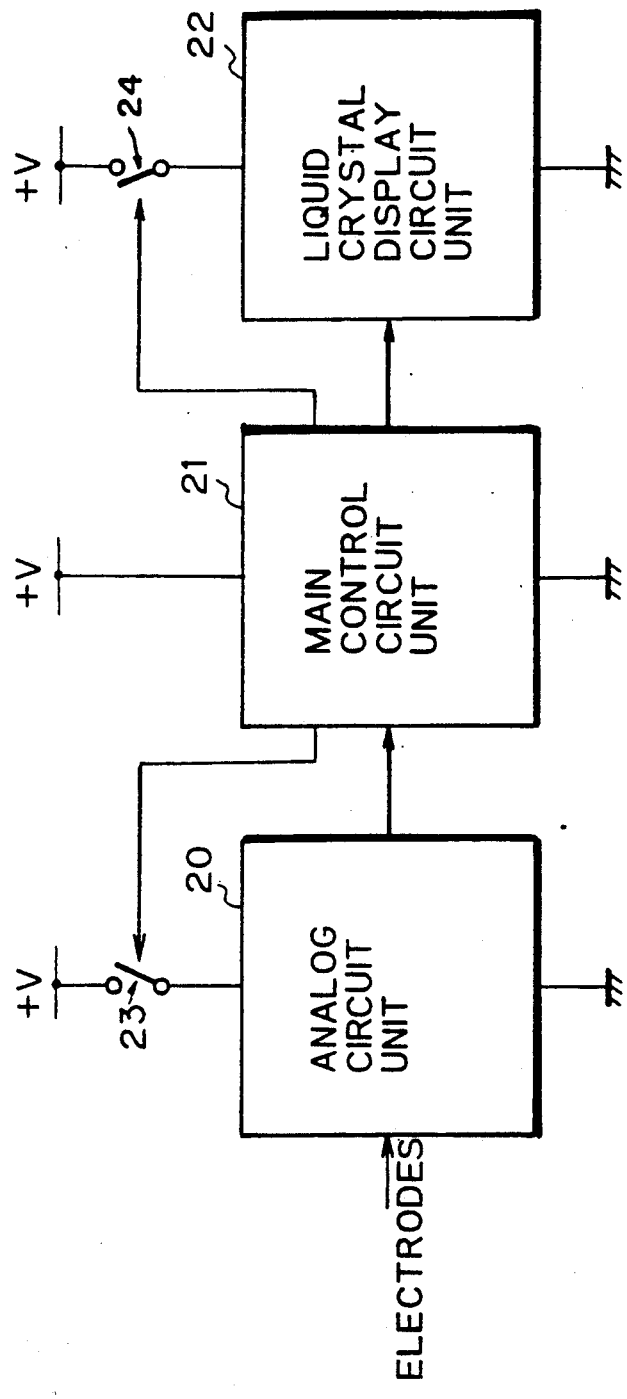
FIG. 5 shows the main circuit of the electrocardiograph shown in FIG. 1.

FIG. 5 shows a block diagram of a main circuit of the portable electrocardiograph according to the present invention. An analog circuit unit 20 includes the electrocardiographic amplifier 12 and the A/D converter 13 shown in FIG. 1 therein, and a power supply terminal thereof is connected to a power supply +V through a switch 23. A main control circuit unit 21 includes the CPU 16, the ROM 18, the RAM 19 shown in FIG. 1 and peripheral circuits therein, and a power supply terminal thereof is always connected to the power supply +V. A liquid crystal display circuit unit 22 includes the liquid crystal display device 14 and the liquid crystal display drive circuit 15 shown in FIG. 1 therein, and a power supply terminal thereof is connected to the power supply +V through a switch 24.

Each of the switches 23, 24 is composed of a software switch which is adapted to be turned on/off by controlling the CPU 16. The switch 23 is turned on in the measurement mode and the measurement start mode, and is turned off in the reproduction mode.

The switch 24 is turned on in the measurement mode and the reproduction mode, and is turned off in the measurement start mode.

Furthermore, enable signal terminals of gate circuits in the units 20, 22 may be used as the switches 23, 24 respectively.

Figure 6B:
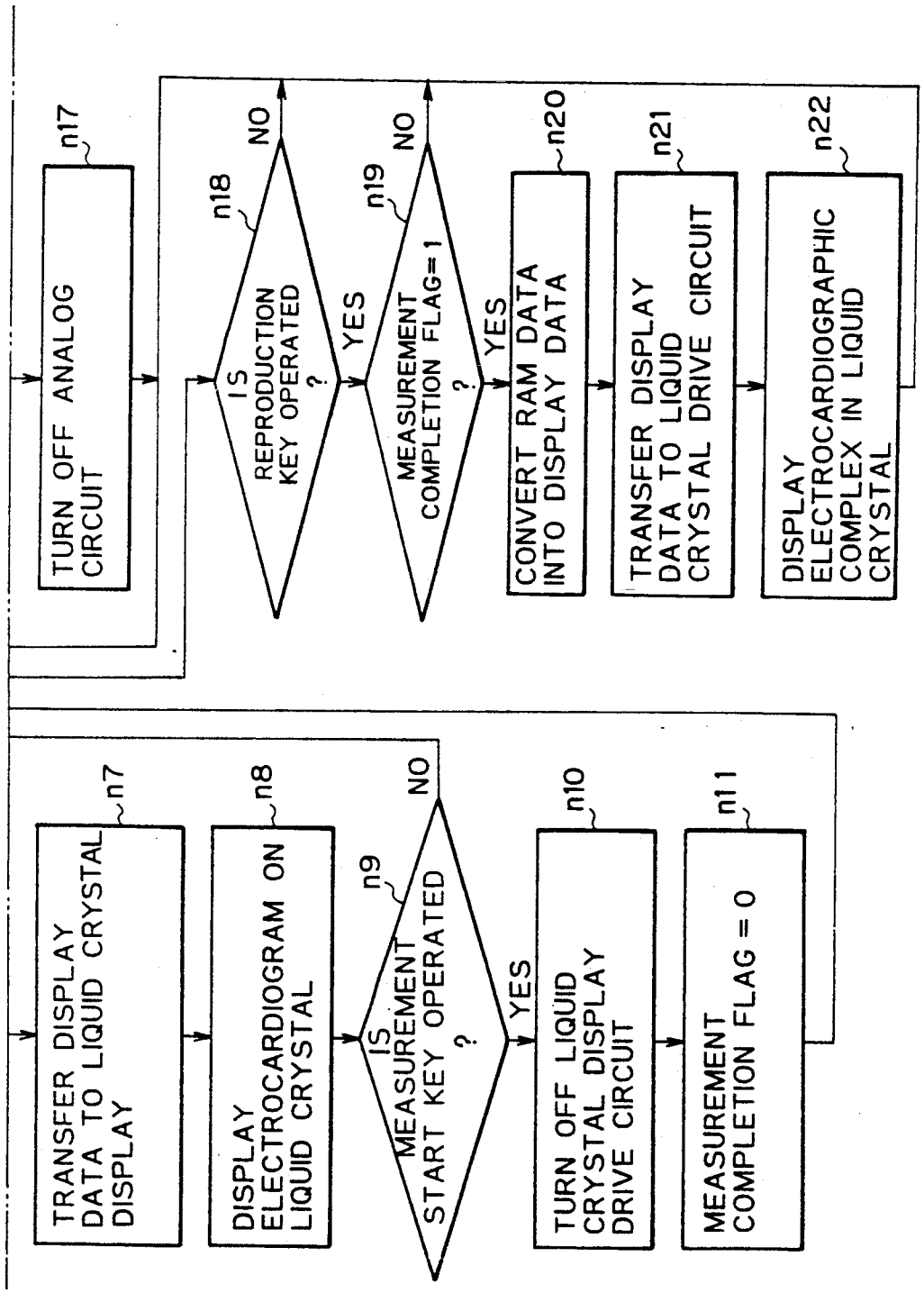
FIG. 6 consisting of FIG. 6a and 6b is a flowchart explaining an operation of the electrocardiograph of FIG. 1.

Specific operations of the portable electrocardiograph of the present invention will now be described according to a flowchart shown in FIG. 6 which consists of FIG. 6a and FIG. 6b.

When this portable electrocardiograph is turned on by operating the power switch 17e (step n1), execution of the flowchart shown in FIG. 6 is started. The CPU 16 drives the switch 44 and supplies electricity to the liquid crystal display circuit unit 22 in order to enable the liquid crystal display circuit unit 22 to be operated (step n2). After the step n2, the electrocardiograph waits for inputs of the measurement key 17a and the reproduction key 17b. At this time, the switch 23 is set in off state and the electricity is not supplied to the analog circuit unit 20.

When the measurement key 17a is operated (step n3), the CPU 16 drives the switch 23 and supplies electricity to the analog circuit unit 20 so as to enable the analog circuit unit 20 to be operated (step n4). With response to this supply of electricity, the electrocardiographic signals detected by the sheet electrode 10 are amplified by the electrocardiographic amplifier 12 and the amplified signals are supplied to the A/D converter 13. The A/D converter 13 samples the amplified signals at a sampling frequency having a predetermined cycle, for example, 250 Hz and outputs digital data (electrocardiographic complex data) in time sequence to the CPU 16 (step n5). The CPU 16 receives the electrocardiographic complex data in time sequence and develops the electrocardiographic complex data into dot data to be used for display and stores the dot data in the display data areas of the RAM 19 (step n6).

Furthermore, the display dot data in the display data areas of the RAM 19 are sequentially transferred to the liquid crystal display drive circuit 15 (step n7), and are displayed in the liquid crystal display device 14 (step n8).

The above operation is repeated until the measurement start key 17c is operated. As a result, the measured electrocardiogram is continuously displayed and observed simultaneously with the measurement as shown in FIG. 7. This electrocardiographic complex data is not stored in the electrocardiographic complex data area of the RAM 19.

Subsequently, when the measurement start key 17c is operated during the above operation (step n9), the CPU 16 turns off the switch 24 so as to stop a drive of the liquid crystal display circuit unit 22 (step n10) and stops the development of the electrocardiographic data into the display dot data. Furthermore, the CPU 16 turns off a measurement completion flag (step n11).

In response to this operation, the measured electrocardiographic complex data is not displayed, but only recorded (stored) after that.

The measured electrocardiographic complex data is sequentially updated and stored in the electrocardiographic complex data area of the RAM 19 (step n12). As described above, in the update and storage, the electrocardiographic complex data X0, X1 . . . is sequentially stored in the data areas from the area with the leading address 0. When the capacity of the data areas are full, a memory loop for sequentially overwriting the data areas from the area with the leading address again is formed. The position, in which the newest data is stored, is always held in the address pointer register and is updated every time when the data is stored.

If an abnormal thing has happened with the body of the subject matter during this operation, the event key 17d is operated so as to hold the electrocardiographic data in a predetermined period before and thereafter (step n13). In response to this operation, the measurement completion flag is turned on (step n14) and the update and the storage are continued for a predetermined time period (step n15). The storage time period corresponds to almost a half of the electrocardiographic complex data area so that the electrocardiographic complex data when the event key is operated is positioned almost in the center of series of data stored in the electrocardiographic complex data area of the RAM 19. After the update and the storage are executed for a predetermined time period, the update and the storage for this area are stopped and the data is stored and held. Furthermore, the switch 24 is turned on so as to enable the liquid crystal display circuit unit 22 to be operated and the switch 23 is turned off so as to stop the measurement operation (step n17), as a consequence the electrocardiograph returns to the above-mentioned initial state.

The user of the portable electrocardiograph may ask his or her physician in charge for a diagnosis by reproducing the above held electrocardiographic complex data in the liquid crystal display device 14. When the reproduction key 17b is operated (step n18), it is judged whether or not the measurement completion flag is on (step n19). If the flag is off, it is judged that there is no measurement data and the key operation is invalidated. If the flag is on, the electrocardiographic complex data in the RAM 19 is read out and displayed in the liquid crystal display device 14 as shown in FIG. 7. In this display operation, the electrocardiographic data is sequentially read out from the area, in which the oldest data is stored, based on the address pointer register, developed into the display dot data (step n20) and transferred to the display data area (step n21). The display dot data in the display data area is supplied to the liquid crystal display drive circuit 15 and displayed (step n22).

As described above, in the portable electrocardiograph of the present invention, the CPU 16 turns on/off the switches 23 and 24 so that the electricity supply to the liquid crystal display device 14 is stopped when the measurement start key is operated and the electricity supply to the electrocardiographic amplifier 12 and to the A/D converter 13 is stopped when the reproduction key is operated.

Many widely different embodiments of the present invention may be constructed without departing from the spirit and scope of the present invention. It should be understood that the present invention is not limited to the specific embodiments described in the specification, except as defined in the appended claims.

What is claimed is:

1. A portable electrocardiograph having a power supply device and capable of providing a low electricity consumption rate by controlling an electric power supply from the power supply device, said portable electrocardiograph comprising:
    means for detecting electrocardiographic signals and for converting said electrocardiographic signals into electrocardiographic complex data;
    means connected with said detecting means for displaying said electrocardiographic complex data;
    means for controlling said electric power supply to selectively connect said electric power supply to said detecting means or said displaying means in accordance with a predetermined mode so that said electric power supply from said power supply device remains connected in such a manner throughout a predetermined time period; and
    means, connected to said detecting means, for storing said electrocardiographic complex data so that said stored electrocardiographic complex data are displayed on said displaying means in accordance with said predetermined mode during said predetermined time period, said predetermined mode being a reproduction mode and where, in accordance with said reproduction mode, said means for controlling disconnects said electric power supply from said power supply device to said detecting means and connects said electric power supply to said means for displaying to display said electrocardiographic complex data stored in said storing means.

2. A portable electrocardiograph according to claim 1, wherein said storing means stores information of a heart pulsation in a precedence time period before activating said reproduction mode thereon.

3. A portable electrocardiograph according to claim 1, wherein said predetermined mode is a storage mode and where, in accordance with said storage mode, said means for controlling disconnects said electric power supply from said power supply device to said displaying means and connects said electric power supply to said means for storing to store said electrocardiographic complex data from said detecting means.

4. A portable electrocardiograph according to claim 1, wherein said portable electrocardiograph further comprises means for supplying said electrocardiographic signals generated in accordance with heart pulsations, and means for amplifying said electrocardiographic signals supplied from said supplying means so that small heart pulsation signals are amplified for detecting any abnormality in said heart pulsations.

5. A portable electrocardiograph according to claim 1, wherein said storing means comprises a plurality of data areas and a plurality of addresses, each of said addresses being attached with each of said data areas, respectively.

6. A portable electrocardiograph according to claim 5, wherein said storing means sequentially arranges said electrocardiographic complex data from an area of said plurality of data areas having an address of said plurality of addresses to another area of said plurality of addresses, said storing means being arranged that a start position and an end position of said electrocardiographic complex data stored therein are judged by holding a data area in a pointer register and said data area holding a newest data in a measurement of said heart pulsations.

7. A portable electrocardiograph according to claim 6, wherein said area of said plurality of data areas is an area having zero address, and said another area of said plurality of data areas is a largest data having address of n−1 with said n representing an integer number.

8. A portable electrocardiograph according to claim 7, wherein said storing means overwrite said plurality of data areas from said data area having said zero address at a time when said electrocardiographic complex data reaches said largest area having said address n−1.

9. A portable electrocardiograph capable of providing a low electricity consumption rate and adapted to be operated in accordance with an electric power supplied by a power supply device, said portable electrocardiograph having electrodes for detecting electrocardiographic signals, said portable electrocardiographic comprising:
    an analog circuit adapted to be connected to said power supply for amplifying said electrocardiographic signals detected by said electrodes and for converting said amplified signals into electrocardiographic complex data;

a main control circuit adapted to be connected to said power supply for receiving said electrocardiographic complex data in a time sequence and for storing dot data developed from said electrocardiographic complex data in display data areas thereof; and a liquid crystal display means adapted to be connected to said power supply for displaying said dot data stored in said display data areas of said main control circuit;

said analog circuit including an electrocardiographic amplifier for amplifying electrocardiographic signals detected by electrodes, an analog/digital converter for sampling said amplified signals at a sampling frequency of a predetermined cycle and for converting said amplified signals into electrocardiographic complex data, and power supply terminals adapted to be connected to said power supply device, switch means for connecting said power supply terminals of said analog circuit to said power supply device, said switch means being composed of a software switch adapted to be turned on/off in accordance with a control of a central processing unit, said switch being adapted to be turned on either in a measurement mode or in a measurement start mode, and to be turned off in a reproduction mode.

10. A portable electrocardiograph according to claim 9, wherein said liquid crystal display means includes power supply terminals, and further including switch means for connecting said power supply terminals of said liquid crystal display means to said power supply device, said switch means being composed of a software switch adapted to be turned on/off in accordance with a control of a central processing unit, and switch being adapted to be turned on either in a measurement mode or in a reproduction mode, and to be turned off in measurement start mode.

11. A portable electrocardiograph according to claim 9, wherein said main control includes a central processing unit for receiving said electrocardiographic complex data in said time sequence and for developing said electrocardiographic complex data into said dot data to be used for display, a random access memory for storing said dot data in display data areas thereof, peripheral circuits therein, and power supply terminals adapted to be connected to said power supply device.

12. A portable electrocardiograph according to claim 11, wherein said liquid crystal display means includes a liquid crystal display device, a liquid crystal drive circuit, and a power supply terminal thereof adapted to be connected to said power supply device.

13. A portable electrocardiograph according to claim 12, wherein said random access memory comprises a plurality of display data areas so that said dot data are sequentially transferred to said liquid crystal display drive circuit and said dot data are displayed in said liquid crystal display device.

* * * * *